United States Patent [19]
Wurster et al.

[11] 4,059,019
[45] Nov. 22, 1977

[54] METHOD AND APPARATUS FOR EXTRACTING GAS SAMPLES OF HIGH TEMPERATURE GASES, PARTICULARLY FOR CEMENT ROTARY KILN FURNACE EXHAUST GASES

[75] Inventors: Winfried Wurster, Bensberg; Jochen Kühne, Horrem; Gerd Frodermann, Solingen, all of Germany

[73] Assignee: Klockner-Humboldt-Deutz Aktiengesellschaft, Germany

[21] Appl. No.: 712,746

[22] Filed: Aug. 9, 1976

[30] Foreign Application Priority Data

Aug. 9, 1975 Germany .............................. 2535646

[51] Int. Cl.$^2$ .............................................. G01N 1/22
[52] U.S. Cl. ................................................ 73/421.5 A
[58] Field of Search ................................... 73/421.5 A

[56] References Cited
U.S. PATENT DOCUMENTS 1,809,325  6/1931  Austin et al. .................... 73/421.5 A
3,643,508  2/1972  Schneider ........................ 73/421.5 A

*Primary Examiner*—S. Clement Swisher
*Attorney, Agent, or Firm*—Hill, Gross, Simpson, Van Santen, Steadman, Chiara & Simpson

[57] ABSTRACT

Gas samples are extracted from a rotary cement kiln type furnace in the area of raw material input and exhaust gas discharge from and to, respectively, a cyclone heat exchanger. The intervening chamber is provided with a door covering a passageway into the chamber through which a gas probe, carried by a gas pick-up device, is extended and retracted. The pick-up device is movably mounted in a guide and is provided with a coolant and apparatus for directing a blast of air to clean the probe immediately prior to withdrawal from the furnace. Emergency controls are provided to sequentially clean the probe, withdraw the probe and close the door for the passageway in response to detection of an adverse condition in at least one operating parameter of the system.

8 Claims, 1 Drawing Figure

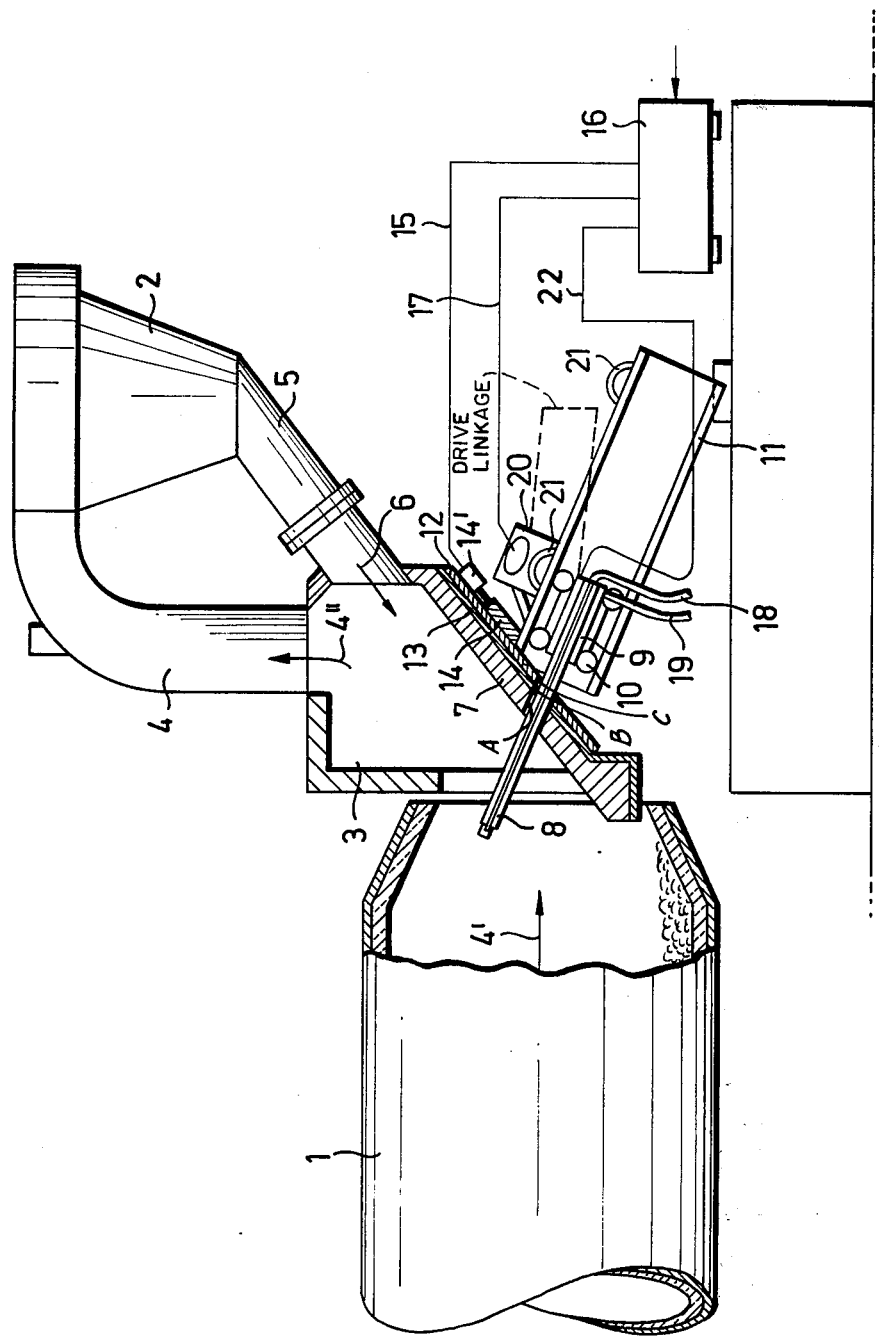

METHOD AND APPARATUS FOR EXTRACTING GAS SAMPLES OF HIGH TEMPERATURE GASES, PARTICULARLY FOR CEMENT ROTARY KILN FURNACE EXHAUST GASES

BACKGROUND OF THE INVENTION

1. Field of the Invention

The present invention relates to gas extraction techniques for highly tempered gases, particularly for rotary kiln furnace exhaust gases in the production of cement, and is particularly concerned with safe and economical methods and apparatus for carrying out the extraction of gas samples.

2. Description of the Prior Art

With the aid of gas extraction apparatus, a representative test portion or sample may be withdrawn from the exhaust gas stream which participates in the combustion process in a rotary furnace, for analysis of gas constituents, in order to thereafter be able to adjudge and regulate the course of the combustion process.

It is known to provide a tubular probe or sampling device fixedly secured with a mounting flange through the wall of the inlet chamber to a rotary furnace, and to utilize such probe or device from time to time to draw off quantities of exhaust gas for analysis of the combustion process. As the probe or sampling device remains constantly in the heated gas chamber, it is disadvantageously subjected to all of the thermal, chemical and mechanical stresses occurring in the chamber. In addition, the continuous presence of the probe or sampling device in the inlet chamber is further disadvantageous, as it favors a deposit formation and bridge formation. It is in this connection both necessary and extraordinarily disadvantageous that the probe or sampling device, upon each cleaning of the heat exchanger, must be dismounted and again remounted with an appreciable expenditure of time. If removal is not undertaken, in a short time the probe or sampling device may be subjected to disturbances by means of material dropping down thereon from upper portions of the apparatus. Furthermore, upon dismounting of the probe or sampling device there always exists an appreciable danger of accident because of the weight of its tip. The reason for this lies both in the length of the probe or sampling device, as well as in the weight which is often increased on one side due to the disadvantageous effect of baking-on or caking of the material undergoing treatment. A further disadvantage resides in the fact that the probe or sampling device, due to a lack of a coolant, i.e., a cooling water supply, become disturbed in short order in the hot atmosphere of the inlet chamber due to the continuous flow of hot exhaust gases therethrough to a cooperating heat exchanger.

SUMMARY OF THE INVENTION

The primary object of the present invention, therefore, is to provide gas extraction techniques, while overcoming or preventing the above known disadvantages, which techniques involve remote actuation, and which ensures with all of the gas samples or specimens necessary for the exhaust gas analysis.

According to the invention, the foregoing object is achieved in that a tubular test probe is fixed in a pick-up device and the pick-up device is transportably mounted for movement in the longitudinal direction of the probe in a guide, which has the advantage that the probe, in case of danger, particularly in the case of repairs in the heat exchanger, may be transported out of the inlet chamber, without having to be dismounted from its pick-up device. With this structure, disturbance of the probe through broken stones dropping down during repair and maintenance is prevented.

In an advantageous development of the invention, it is provided that a drive is connected to and operated for moving the pick-up device in the guide. In this manner, the probe, upon each cleaning of the heat exchanger, may be transported out prior to cleaning and remain ready for operation in the pick-up device and guide structure, so that only after conclusion of the cleaning and when an analysis is required, the probe may again be transported to an operational position within the inlet. In this manner, the life of the device is advantageously prolonged, as the probe must remain in the heating gas chamber only for the particular short measuring operation, and is only subjected to the deleterious effects of the aggressive media during this short time in the chamber.

In a further development of the invention, the drive is automatically actuatable by remote control and is provided with an emergency control for the independent transportation of the probe out of the hot gas chamber, whereby the protection of the sensitive implement is increased and the securing of the device is set independently of the attention of operating personnel.

In a further development of the invention, upon conveyance of the probe, a locking flap or valve is actuated to close the passageway to the heating gas chamber. This measure serves for securing the operating level, because an outflow of hot charging material or of heating gas is prevented and, secondly, the sucking in of unfiltered air during the process is prevented.

Furthermore, for an additional development of the invention, it is provided that, upon the conveyance of the probe, a blowing apparatus, e.g., air pressure jet, is actuated, whereby deposits of dust and the like may be removed and eventual depositing and damming up of material may be prevented, in order to lower the mechanical strain of the probe upon conveying the same in and out of the inlet chamber.

In order to ensure automation of the gas extraction operation, and to be able to actuate the apparatus independently of operating personnel, an energy storage device having an emergency control is provided for independent transportation of the probe out of the chamber and closure of the heating chamber locking flap. In this manner, the locking flap (door) to the heating chamber is, in each case, opened shortly before the beginning of the entry movement and immediately closed again after withdrawal of the probe, and always after the exit of the tip of the probe.

In a further development of the invention, it is recommended that the guide of the probe be hingedly attached to a mounting plate. With this construction, the mounting and adjusting of the guide is appreciably facilitated upon installation and, in the case of a repair of upon a change of the probe, the removal or also maintenance work on the probe, the same may be better accessible and the work may be carried out more rapidly because the guide may be swung out of the way of the remainder of the apparatus. A probe exchange is possible at the point of entry without dismounting of the entire apparatus.

BRIEF DESCRIPTION OF THE DRAWING

Other objects, features and advantages of the invention, its organization, construction and operation will be best understood from the following detailed description taken in conjunction with the accompanying drawing, on which there is a single FIGURE, shown partially in section, of the raw material inlet end of a rotary kiln furnace, the apparatus for carrying out extraction of gas samples being specifically illustrated.

DESCRIPTION OF THE PREFERRED EMBODIMENTS

Referring to the drawing, the inlet end of a rotary furnace 1 for cement production is illustrated as having a platform on which a device for gas extraction is mounted. The rotary furnace 1 and a heat exchanger 2, which may be a well known cyclone heat exchanger, are connected in communication by means of an inlet chamber 3. From the inlet chamber 3, an exhaust gas pipe 4 extends to the heat exchanger, a pipe 5 having a swinging flap closure connects the lower cyclone tip of the heat exchanger 2 to the inlet chamber 3, and the rotary kiln and inlet chamber have openings for the passage of raw material charging and exhaust gas discharging. An arrow 6 symbolically indicates the direction of the feed of pulverized raw material from the heat exchanger to the rotary furnace, it being apparent that the material flows over a wall 7 of the heat exchanger, which wall extends through the input opening of the furnace 1.

In the pipe 5, the fine, preheated, pulverized raw material is supplied through the hot furnace exhaust gases to the rotary furnace 1.

In order to determine the operational condition of the furnace, analysis of the combustion gases is required, in addition to the knowledge of other parameters. The combustion gases flow along the path indicated by the arrows 4' and 4'' out of the rotating furnace 1 and into the stationary heat exchanger 2. A gas extraction probe 8 is inserted through an opening A in the inclined wall 7 of the inlet chamber 3 and is therefore suitably directed so that it projects in such a manner that its tube extends into the rotary furnace, particularly the hot gas flow, and may withdraw sample from the stream of combustion gases.

The probe 8 is fixed in a pick-up device 9 which, on its part, is connected in a carriage 10. The carriage 10 is movably mounted in a guide 11 to ensure a movement in the longitudinal direction of the probe. The carriage is connected with a drive which is actuated by or from the control room. The guide 11 is connected to a mounting plate 12 which is connected in a suitable manner with an outer sleeve 13 of the inlet chamber 3, the mounting plate 12 including an opening B aligned with the opening A and the outer sleeve 13 including an opening C aligned with the openings A and B to define a passageway for access to the rotary furnace. Above the passageway A, B, C a blocking flap 14 having an actuating apparatus 14' is provided to block the passageway. The blocking flap is provided with a guide carried by the mounting plate 12 (not shown) for movement from the position illustrated to a position to cover the passageway.

A conduit 15 connects the actuating apparatus 14' to an emergency assembly having its own actuating control, for example in the form of a pneumatic energy storage device 16. A further conduit 17 connects the energy storage device 16 with a drive 20 for movement of the probe from the operating position into the resting position. A further group of conduits is illustrated by means of a line 22; and it is through these conduits, in the case of necessity, that a blast of air is directed toward the probe. Upon loss of cooling water or energy, or in the case of a disturbance in the furnace, the emergency assembly, which includes sensors for sensing such parameters, automatically acts in response to predetermined levels of the parameters to generate a control signal. In response to this control signal the conduits 22, 17 and then 15 are consecutively activated in order to blow free the probe, withdraw the probe out of the heating gas chamber, and then close the passageway to the inlet chamber 3 by means of operating the blocking flap 14. In this manner, the transporting assembly drive and the mechanism of the blocking flap are uncoupled and a blocking interpolated, for whose release the energy storage device 16 must again be fully filled before the probe can again be moved into the chamber after the disturbance has been overcome.

On the drawing, the operating position is illustrated in which the probe 8 is conveyed through the passageway in the inclined wall 7 of the inlet chamber 3 and finds itself in the heating gas chamber in order to extract the gas samples necessary for gas analysis.

The gas samples are withdrawn through a pipe or tube conduit, to which are attached the flexible tubes 18, and conveyed to a filter and analyzing device (not illustrated). Additional tube feeds, symbolized by the tube 19, are provided for the pressurized air and liquid feed, as well as for the inflow and outflow of the circulation of coolant, for cooling the probe within the heating chamber pressurized air and liquid feeds are provided for cleaning and blowing free of the probe 2 and for the preparation and removal of deposits over the probe passageway in the inlet chamber wall 7. By means of a pressurized air free blowing apparatus, the probe, upon conveyance into the heating gas chamber is protected from mechanical strain. Thereby, these air pressure conduits, independently of those of the emergency flow aggregate 16, automatically take over only in case of emergency, for example with loss of cooling water and flow, automatically conveying the probe out of the chamber and conveying the tip beyond the blocking flap 14 for protection of the device.

The drive for moving the pick-up device 9 is constructed in the guide 11 in a conventional manner, as a motor-driven mechanism having a chain drive, for example, among other types of drives which may be utilized. The drive may, however, also take place with hydraulic or pneumatic means and correspond with the operational conditions of the particular installation. The drive or actuating apparatus 14' for closing the passageway to the heating gas chamber by moving the blocking flap 14 may be derived in a suitable manner by means of a motor; however, the drive may be provided through a spring-force storage having a coupling from the drive for conveying the probe. The guide is provided with eyelets 21 which serve as aids in mounting the guide upon installation at the site. Upon exchange of a probe tube, the entire guide 11 is swingable with the device fixed therein about the pivotal connection of the guide 11 with the mounting plate. In a mounting position facilitated by means of such a swinging connection, advantageously the probe exchange is made possible without dismounting and removing the device at the point of installation.

Although we have described our invention by reference to a particular illustrative embodiment thereof, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

We claim:

1. Apparatus for obtaining gas samples from the exhaust gases of a rotary kiln furnace having an exhaust gas outlet, comprising:
   gas sampling means including a gas sample pick-up device which comprises an elongate gas sampling probe;
   guide means mounting said pick-up device for movement in the longitudinal direction of said probe for disposition of said probe within and without of the exhaust gas outlet of the furnace;
   drive means connected to said pick-up device for driving the same along said guide means;
   remote control means connected to operate said drive means; and
   means for sensing at least one operating parameter and independently operating said drive means to withdraw said probe upon sensing a predetermined value of that parameter.

2. Apparatus for taking gas samples from the exhaust gases of a rotary kiln, comprising:
   a rotary kiln including an opening for discharging exhaust gases and receiving raw material;
   a heat exchanger for preheating the raw material, said heat exchanger including an exhaust gas inlet, a raw material inlet and a raw material outlet;
   walls connected together to define a raw material inlet chamber connecting said rotary kiln opening with said exhaust gas inlet and said raw material outlet of said heat exchanger;
   a passageway through one of said walls;
   gas sampling means outside of said chamber including a gas pick-up device and a gas sampling probe carried by said gas pick-up device;
   control means for moving said gas pick-up device including a drive motor connected to said pick-up device;
   guide means mounting said pick-up device for movement toward and away from said chamber to dispose said probe, through said passageway, into and out of the exhaust gas flow of said furnace; and
   door means for closing said passageway when said probe is withdrawn,
   sensing means in said control means for sensing at least one operating parameter and responsive to a predetermined value of that parameter to produce a control signal, and
   emergency operating means in said control means and connected to said sensing means and to said door means and said drive motor and responsive to said control signal to cause withdrawal of said probe and closure of said passageway.

3. The apparatus of claim 2, comprising:
   pivotal mounting means mounting said guide means so that the same may be rotated away from said chamber for maintenance purposes.

4. The apparatus of claim 2, wherein said sampling means comprises means supporting a flow of coolant to said probe.

5. The apparatus of claim 2, comprising:
   cleaning means for supporting a flow of cleaning fluid to the tip of said probe.

6. The apparatus of claim 2, comprising:
   cleaning means connected to said emergency operating means and responsive to said control signal to support a flow of cleaning fluid to the tip of said probe prior to withdrawal of said probe.

7. A method of taking gas samples from the exhaust gases of a rotary kiln furnace, comprising the steps of:
   inserting a gas sampling probe from outside of the furnace into the exhaust gas flow of the furnace;
   feeding a gas sample from the probe to gas analyzing equipment outside of the furnace; and
   withdrawing the probe from the furnace.

8. A method of taking gas samples of the exhaust gases of the furnace which has a door to provide access to the flow of the exhaust gases, comprising the steps of:
   opening the door;
   inserting a gas sampling probe through the door and into the flow of exhaust gas;
   transporting a gas sample from the probe to an external gas analyzer while contemporaneously cooling the probe;
   flowing a cleaning agent over the tip of the probe by directing a blast of compressed air at the tip of the probe;
   withdrawing the probe from the furnace;
   closing the door to prevent the escape of exhaust gas and heat and the introduction of unfiltered air; and
   monitoring at least one system parameter and immediately causing the sequential steps of flowing a cleansing agent, withdrawing the probe and closing the door upon detection of a predetermined value of that parameter.

* * * * *